United States Patent [19]

Tokuda et al.

[11] Patent Number: 5,449,623

[45] Date of Patent: Sep. 12, 1995

[54] METHOD FOR MEASURING BILIRUBIN

[75] Inventors: Kuniaki Tokuda, Kawagoe; Kazuhito Tanimoto, Sakai, both of Japan

[73] Assignee: Wako Pure Chemical Industries, Ltd., Osaka, Japan

[21] Appl. No.: 312,003

[22] Filed: Sep. 23, 1994

Related U.S. Application Data

[63] Continuation of Ser. No. 77,956, Jun. 18, 1993, abandoned, which is a continuation of Ser. No. 783,297, Oct. 28, 1991, abandoned.

Foreign Application Priority Data

Oct. 30, 1990 [JP] Japan .................. 2-293227

[51] Int. Cl.$^6$ .................................... G01N 33/00
[52] U.S. Cl. ............................ 436/97; 436/164
[58] Field of Search ............... 436/12, 63, 97, 164, 436/815; 435/25

[56] References Cited

U.S. PATENT DOCUMENTS

| | | | |
|---|---|---|---|
| 4,115,064 | 9/1978 | Girdler | 436/97 |
| 4,288,343 | 9/1981 | Louderback | 436/97 |
| 4,311,483 | 1/1982 | Perry | 436/97 |
| 4,404,286 | 9/1983 | Shull | 436/97 |
| 4,820,416 | 4/1989 | Chang et al. | 436/97 |
| 5,104,794 | 4/1992 | Kondo et al. | 435/25 |

FOREIGN PATENT DOCUMENTS

| | | |
|---|---|---|
| 0160239 | 11/1985 | European Pat. Off. . |
| 0387784 | 9/1990 | European Pat. Off. . |
| 2505048 | 4/1982 | France . |

OTHER PUBLICATIONS

Derwent Publications Ltd., JP-A 59 160,764, Amano Pharm. K.K., Sep. 1984.
Database WPIL Derwent Publications Ltd., London, GB; Database WPIL, Assession No. 85-090650, Week 8515; & JP-A-60040957, (Toyobo KK), 4 Mar. 1995, *Abstract*.
Clinica Chimica Acta, 62, (1975), 169–172.
Inorganica Chimica Acta, 106, (1985), 181–186.
Clin. Biochem., 21, (1988), 33–38.

*Primary Examiner*—James C. Housel
*Assistant Examiner*—Maureen M. Wallenhorst
*Attorney, Agent, or Firm*—Armstrong, Westerman, Hattori, McLeland & Naughton

[57] ABSTRACT

Total or direct bilirubin can be measured stably with high reliability by using as an oxidizing agent vanadic acid ions or manganese (III) ions, or direct bilirubin can also be measured by using as a reaction inhibitor a water-soluble high polymer or a nonionic surfactant having a HLB value of 15 or more.

21 Claims, 2 Drawing Sheets

METHOD FOR MEASURING BILIRUBIN

This application is a continuation of application Ser. No. 08/077,956 filed Jun. 18, 1993, now abandoned, which was a continuation of Ser. No. 07/783,297, filed Oct. 28, 1991, abandoned.

BACKGROUND OF THE INVENTION

This invention relates to a method for measuring bilirubin contained in a living body fluid such as plasma, serum, urine or the like.

Bilirubin is a compound derived from hemoglobin liberated by lysis of aged erythrocyte. Blood of a living body contains direct bilirubin (mainly glucuronide conjugate form) which reacts directly with a diazo compound to develop a color, and indirect bilirubin (free form) which reacts with a diazo compound only in the presence of an accelerator such as an alcohol.

Diagnoses of various liver diseases and diacrisis of jaundice can be made by measuring total bilirubin concentration and the concentration of each of the above two forms of bilirubin in blood, and hence the measurement of bilirubin is an important examination among clinical examinations.

At present, a leading method for measuring bilirubin is the so-called diazo method which comprises measuring the purplish red color of azobilirubin formed by the reaction of bilirubin with a diazo compound. The diagnoses of various liver diseases and the diacrisis of jaundice are made on the basis of the concentrations of bilirubins measured mainly by this method. This method, however, is disadvantageous, for example, in that reagent solutions for the method can be used for only about 5 days after their preparation, and that measured values are affected by L-ascorbic acid and hemoglobin which are present in a sample.

As other methods for measuring bilirubin, there can be exemplified BOD method utilizing bilirubin oxidase (BOD) as an oxidizing agent, high-performance liquid chromatography method utilizing high-performance liquid chromatography, film method comprising measuring $\alpha$, $\beta$, $\gamma$ and $\delta$ forms of bilirubin by use of a film coated with a mordant, and chemical oxidation method using ferricyanide ions or copper ions as an oxidizing agent (e.g. a method for measuring total or direct bilirubin by use of potassium ferricyanide, a method for measuring direct bilirubin by use of copper ions and thiourea, etc.). All of these methods involve some problem and cannot be said to be preferable to the diazo method. In detail, the BOD method involves no particular problem when used for measuring total bilirubins, but is disadvantageous in that when it is used for measuring direct bilirubin, the measurement should be carried out at a pH outside the optimum pH range for BOD, so that a large amount of the enzyme is unavoidably needed, resulting in a high cost of the measurement. The high-performance liquid chromatography method and the film method are rated high in the precision of measurement but are disadvantageous, for example, in that they require an apparatus for exclusive use and cannot be utilized for measuring many items at the same time for a large number of samples. In the case of the chemical oxidation method, total bilirubins and direct bilirubin cannot be measured at the same pH, so that the measurement is influenced by a change of the absorption curve of bilirubin which accompanies a pH change. Therefore when direct bilirubin is measured utilizing an absorbance value measured by use of standard solutions at the time of measuring total bilirubins, the reliability of measured values is lowered. Furthermore, the BOD method and the chemical oxidation method are disadvantageous also in that a measured value of direct bilirubin obtained by these methods is in poor correlation with that obtained by the diazo method, and hence is difficult to utilize for diagnoses of various liver diseases and diacrisis of jaundice which have been established on the basis of measured values obtained by the diazo method.

Under such circumstances, there is desired a method for measuring bilirubin which can be applied to an automatic analyzer, is in good correlation with the diazo method, and is excellent in the stability of reagent solutions.

SUMMARY OF THE INVENTION

This invention was made in consideration of such conditions and is intended to provide a method for measuring billrubin which can be applied to an automatic analyzer, is in good correlation with the diazo method, is excellent in the stability of reagent solutions, and can give measured values little affected by substances present in a sample together with bilirubin.

This invention provides a method for measuring total or direct bilirubin which comprises adding a reagent solution comprising vanadic acid ions or manganese (III) ions as an oxidizing agent to a sample of living body fluid, and measuring an optical change of the sample fluid.

This invention also provides a method as mentioned above, wherein direct bilirubin is measured by further using at least one compound selected from the group consisting of hydrazine derivatives, hydroxylamine derivatives, oximes, aliphatic polyvalent amines, phenols, water-soluble high polymers, and nonionic surfactants having a HLB value of 15 or more.

This invention further provides a method for measuring direct bilirubin which comprises adding a reagent solution comprising a chemical oxidizing agent and at least one compound selected from the group consisting of hydrazine derivatives, hydroxylamine derivatives, oximes, aliphatic polyvalent amines, phenols, water-soluble high polymers, and nonionic surfactants having a HLB value of 15 or more, as a reaction inhibitor to a sample of living body fluid, and measuring an optical change of the sample fluid.

This invention still further provides a method for measuring direct bilirubin which comprises adding a reagent solution comprising bilirubin oxidase and at least one compound selected from the group consisting of water-soluble high polymers and nonionic surfactants having a HLB value of 15 or more as a reaction inhibitor to a sample of living body fluid, and measuring an optical change of the sample fluid.

BRIEF DESCRIPTION OF THE DRAWINGS

FIG. 1 and FIG. 2 show correlation graphs obtained on the basis of measured values obtained by Example 1 and Referential Example 1.

DESCRIPTION OF THE PREFERRED EMBODIMENTS

As the vanadic acid ions used in the method for measuring bilirubin of this invention, any vanadic acid ions can be exemplified without particular limitation so long as they can be used for the object of this invention. Preferable specific examples of the vanadic acid ions are those containing pentavalent vanadium, such as $VO_3^-$, $VO_4^{3-}$, etc. When the vanadic acid ions are added to a reagent, vanadic acid itself may be used, though it is preferable from the viewpoint of the solubility, etc. to use vanadic acid in the form of a salt, for example, a salt with an alkali metal such as lithium, sodium, potassium or the like, or an ammonium salt.

As the manganese (III) ions used in the method for measuring bilirubin of this invention, there can be exemplified not only those forming common manganese (III) salts such as manganese (III) acetate, but also those forming chelates with chelating agents such as acetylacetone, ethylenediaminetetraacetic acid, etc.

Although the concentration of the vanadic acid ions or manganese (III) ions used for measuring bilirubin is not critical so long as it is such that bilirubin in a sample can be oxidized, the concentration of the vanadic acid ions or manganese (III) ions in a mixture of a sample and all reagent solutions used (hereinafter referred to as "total reagents mixture") is usually 0.02 to 10 mg ions/liter, preferably 0.1 to 2 mg ions/liter.

In the method for measuring direct bilirubin of this invention, as the reaction inhibitor which has an ability to prevent indirect bilirubin from oxidization by an oxidizing agent, there are used one or more compounds selected from the group consisting of hydrazine derivatives, hydroxylamine derivatives, oximes, aliphatic polyvalent amines, phenols, water-soluble high polymers, and nonionic surfactants having a HLB value of 15 or more. As these compounds, any compounds can be used without particular limitation so long as they do not affect the measurement of direct bilirubin.

Preferable specific examples of the hydrazine derivatives are hydrazine, phenylhydrazine and mineral acid salts (hydrochlorides, sulfates, etc.) thereof.

The hydroxylamine derivatives include, for example, hydroxylamine, phenylhydroxylamine, and mineral acid salts (hydrochlorides, sulfates, etc.) thereof.

The oximes include, for example, acetoxime, diacetylmonooxime and salicylaldoxime.

The aliphatic polyvalent amines include, for example, tetraethylenepentamine, hexamethylenetetramine and triethylenetetramine.

Preferable specific examples of the phenols are phenol, p-chlorophenol, p-acetamidophenol, 4-chloro-1-naphthol and β-naphthol.

Preferable specific examples of the water-soluble high polymers are polyvinyl alcohols and polyvinyl pyrrolidones.

The nonionic surfactants having a HLB value of 15 or more include, for example, Emalgen-123P (a polyoxyethylene lauryl ether, a trade name, Kao Corp.), Emalgen-950 (a polyoxyethylene nonylphenyl ether, a trade name, Kao Corp.), Emalgen-985 (a polyoxyethylene nonylphenyl ether, a trade name, Kao. Corp.) and Triton X-405 (a polyoxyethylene isooctylphenyl ether, a trade name, Rohm and Haas Co.).

Although these reaction inhibitors have an inhibitory effect on the oxidation of indirect bilirubin even when used singly, a combination of two or more of them has a higher inhibitory effect on the oxidation of indirect bilirubin in some cases. Therefore, they may be properly chosen depending on purposes. Although the concentration of the reaction inhibitor used for measuring direct bilirubin is not critical so long as it is such that the oxidation of indirect bilirubin can be inhibited, and the concentration depends on the kind of the compound(s) used as reaction inhibitor, the concentration of the reaction inhibitor in a total reagents mixture is usually 0.01 to 5 w/v %.

In any method for measuring direct bilirubin by a chemical oxidation method which comprises adding a chemical oxidizing agent to a sample of living body fluid and measuring an optical change such as the degree of change of the color, of the sample fluid, the above-exemplified reaction inhibitors according to this invention can be effectively used regardless of the kind of the chemical oxidizing agent. Of these reaction inhibitors, the water-soluble high polymers and the nonionic surfactants having a HLB value of 15 or more can be used as reaction inhibitors also for measuring direct bilirubin by use of bilirubin oxidase.

The presence of a chelating agent in a reagent solution used in this invention is preferable, because it lowers a reagent blank value to improve the precision of analysis, stabilizes the reagent solution, and accelerates the oxidation reaction of bilirubin. Preferable specific examples of the chelating agent used for such purposes are ethylenediaminetetraacetic acid (EDTA), nitrilotriacetic acid (NTA), cyclohexanediaminetetraacetic acid (CyDTA), diethylenetriaminepentaacetic acid (DTPA), hydroxyethylethylenediaminetetraacetic acid (EDTA-OH), triethylenetetraminehexaacetic acid (TTHA), hydroxyethylimino-diacetic acid (HIDA), 1-hydroxyethane-1,1-diphosphonic acid, and alkali metal salts (e.g. lithium salts, sodium salts and potassium salts) thereof and ammonium salts thereof. Although the concentration of the chelating agent used for measuring bilirubin is not critical so long as it does not hinder the measurement of bilirubin, the concentration of the chelating agent in a total reagents mixture is usually 0.02 to 50 mM, preferably 1 to 30 mM, and more preferably 1 to 20 mM.

When total bilirubin concentration is measured by the method of this invention, the presence of a conventional bilirubin oxidation reaction accelerator (hereinafter abbreviated merely as "reaction accelerator") in a reagent solution is preferable because it reduces the measurement time. As the reaction accelerator used for such a purpose, there can be exemplified all reaction accelerators usually used in the art for such a purpose, for example, anionic surfactants such as sodium lauryl sulfate, sodium lauryl benzenesulfonate, sodium cholate, etc.; cationic surfactants such as cetyltrimethylammonium bromide, cetylpyridinium chloride, etc.; and alkylbetaine type amphoteric surfactants such as Amphitol-24B (a trade name, Kao Corp.), etc. Of these reaction accelerators, the amphoteric surfactants are particularly preferable because they can be utilized in a wide pH range of 2 to 13 and have a high clarifying effect on chylous serum. Although the concentration of the reaction accelerator used for measuring bilirubin is not critical so long as it is such that the oxidation of bilirubin in a sample can be accelerated, the concentration of the reaction accelerator in a total reagents mixture is usually 0.01 to 3 w/v %, preferably 0.1 to 2 w/v %.

Other reagents (e.g. buffers and antiseptics) used in the measuring method of this invention may, if necessary, be properly selected, for example, from buffers such as phosphoric acid, citric acid, succinic acid, etc., and antiseptics which are used, for instance, in per se well-known chemical oxidation method and BOD method. It is sufficient that the concentration of these reagents, the pH's of reagent solutions, etc. are properly determined in accordance with those employed for reagent solutions used in the per se well-known methods.

This invention is conducted, for example, as follows.

When total bilirubin concentration is measured, a buffer solution containing a reaction accelerator and optionally a chelating agent and the like is first prepared as a first reagent solution, and then mixed with a sample containing bilirubin, for example, a living body fluid such as plasma, serum, urine or the like, and absorbance at a specific wavelength (about 430 to about 460 nm) of the resulting solution is measured (absorbance 1). Subsequently, a second reagent solution containing vanadic acid ions or manganese (III) ions and optionally a chelating agent is added, and the oxidation reaction of bilirubin is carried out at 25° to 40° C. for 3 to 15 minutes, after which absorbance at the specific wavelength is again measured (absorbance 2). The thus obtained values of absorbance 1 and absorbance 2 are, for example, multiplied by a correction factor for solution volume, etc., and then the difference of absorbance at the specific wavelength before and after the oxidation reaction is calculated. The total bilirubin concentration in the sample can be determined by using this calculated value and a calibration curve showing the relationship between bilirubin concentration and the change of absorbance at the specific wavelength which has previously been prepared by the same procedure as above by using standard solutions of known bilirubin concentrations.

For measuring direct bilirubin concentration, a buffer solution containing the reaction inhibitor and optionally a chelating agent and the like is used as a first reagent solution, and the same solution as the above second reagent solution for measuring total bilirubin concentration can be used as a second reagent solution. Except for using the first and second reagent solutions described above, the same procedure as for the measurement of total bilirubin concentration can be carried out.

Total bilirubin concentration or direct bilirubin concentration in a sample can be measured also by the same procedure as the above procedure of measuring total bilirubins or direct bilirubin, except for using as absorbance 1, absorbance measured for a solution obtained by mixing a portion of the first solution with a portion of the sample, and as absorbance 2, absorbance measured for a solution obtained by reacting another portion of the sample with a previously prepared mixture of another portion of the first solution and the second solution.

As mentioned above, the reaction inhibitor according to this invention can be effectively used in per se well-known chemical oxidation method, for example, such as chemical oxidation method using ferricyanide ions or copper ions as a chemical oxidizing agent. Therefore, when a buffer solution containing the reaction inhibitor according to this invention and optionally a chelating agent is used as a first reagent solution and a buffer solution containing these chemical oxidizing agent such as ferricyanide ions, copper ions, etc. and optionally a chelating agent is used as a second reagent solution, direct bilirubin concentration can also be measured in good correlation with the diazo method by the same procedure described above.

Furthermore, of the reaction inhibitors used in this invention, the water-soluble high polymers and the nonionic surfactants having a HLB value of 15 or more can be used as a reaction inhibitor in a method for measuring direct bilirubin by use of bilirubin oxidase. Therefore, when a buffer solution containing this compound as a reaction inhibitor and optionally a chelating agent is used as a first reagent solution and a buffer solution containing bilirubin oxidase and optionally a chelating agent is used as a second reagent solution, direct bilirubin concentration can also be measured in good correlation with the diazo method by the same procedure described above.

In the each method for measuring direct bilirubin mentioned above, nonionic surfactants having a HLB value of less than 15 cannot be used.

This is because the nonionic surfactant having such a property cannot prevent the oxidation of indirect bilirubin sufficiently, resulting in providing a measured value of direct bilirubin poor in correlation with that obtained by the diazo method. This arises a problem in practical use.

This invention is more concretely explained below with reference to Experimental Examples and Examples, which are not by way of limitation but by way of illustration.

Experimental Example 1

Selection of an oxidizing agent for bilirubin

The following experiment was carried out for finding metal ions useful as an oxidizing agent for bilirubin.

[Reagent solutions]

First reagent solution 0.1M acetic acid-sodium acetate buffer (pH 4.0) was used as a first reagent solution (R1, hereinafter the same applied).

Second reagent solution 0.1M acetic acid-sodium acetate buffer (pH 4.0) containing 1 mM predetermined metal ions was used as a second reagent solution (R2, hereinafter the same applied).

[Samples]

An aqueous solution containing ditaurobilirubin in an amount corresponding to 10 mg/dl of bilirubin was used as a direct-bilirubin-containing sample, and commercially available bilirubin standard serum (containing 10 mg/dl of indirect bilirubin, available from Wako Pure Chemical Industries, Ltd.) was used as an indirect-bilirubin-containing sample.

[Procedure]

Measurement was carried out by use of a Hitachi automatic analyzer Model 7050 (mfd. by Hitachi, Ltd.) under the conditions shown in Table 1.

TABLE 1

| CHEMISTRY PARAMETERS | |
| --- | --- |
| ASSAY CODE | [2POINT]:[15]-[32] |
| SAMPLE VOLUME | [15] |
| R1 VOLUME | [400][50][NO] |
| R2 VOLUME | [100][50][NO] |
| WAVE LENGTH | [505][450] |
| CALIB. METHOD | [LINEAR ][0] |
| STD. (1) CONC.-POS. | [0.0]-[1] |
| STD. (2) CONC.-POS | [10.0]-[2] |
| STD. (3-6) CONC.-POS | [0]-[0] |
| UNIT | [MG/DL] |
| SD LIMIT | [0.1] |
| DUPLICATE LIMIT | [10000] |
| SENSITIVITY LIMIT | [0] |
| ABS.LIMIT(INC/DEC) | [0][DECREASE] |
| PROZONE LIMIT | [0][LOWER] |
| EXPECTED VALUE | [0]-[10000] |
| INSTRUMENT FACTOR | [1.00] |

[Results]

TABLE 2

| Metal ions | Blank value | Direct-bilirubin-containing sample | Indirect-bilirubin-containing sample |
|---|---|---|---|
| | | OD (505 nm/450 nm) | |
| $[Fe(CN)_6]^{-3}$ | 0.030 | 0.265 | 0.088 |
| $Co^{2+}(CoCl_2)$ | 0.000 | 0.034 | 0.068 |
| $V^{4+}(VOSO_4)$ | 0.000 | 0.031 | 0.068 |
| $V^{5+}(NaVO_3)$ | 0.048 | 0.329 | 0.065 |
| $Mn^{2+}$(acetate) | 0.000 | 0.022 | 0.065 |
| $Mn^{3+}$(acetate) | 0.024 | 0.299 | 0.096 |
| $Cu^{2+}(CuSo_4)$ | 0.000 | 0.079 | 0.070 |
| $Fe^{3+}$(iron alum) | 0.040 | 0.167 | 0.059 |
| $Ni^{2+}(NiSO_4)$ | 0.000 | 0.091 | 0.088 |

As is clear from the results shown in Table 2, ferricyanide ions, metavanadic acid ions and manganese (III) ions are excellent as oxidizing agents. However, ferricyanide ions which are ions of a cyanide are disadvantageous from the viewpoint of the disposal of a waste solution, and therefore of the above three kinds of ions, metavanadic acid ions and manganese (III) ions are judged to be highly useful for practical purposes.

Experimental Example 2

Examination of indirect bilirubin reaction inhibitors which have an ability to prevent indirect bilirubin from oxidization by an oxidizing agent.

A hydrazine derivative, a hydroxylamine derivative, oximes, an aliphatic polyvalent amine, a phenol, a water-soluble high polymer and a nonionic surfactant having a HLB value of 15 or more were examined for ability to inhibit the oxidation reaction of indirect bilirubin.

[Reagent solutions]

First reagent solution

As a first reagent solution, there was used 0.1M citric acid-sodium citrate buffer (pH 3.0) containing predetermined concentration of one or two compounds selected from the group consisting of the hydrazine derivative, hydroxylamine derivative, oximes, aliphatic polyvalent amine, phenol, water-soluble high polymer, and nonionic surfactant having a HLB value of 15 or more, and 0.2% EDTA·2Na.

Second reagent solution (manganese method)

As a second reagent solution for manganese method, there was used 0.01M phosphate buffer (pH 6.0) containing 3 mM manganese (III) acetate and 0.2% EDTA·2Na.

Second reagent solution (vanadic acid method)

As a second reagent solution for vanadic acid method, there was used 0.01M phosphate buffer (pH 6.0) containing 3 mM sodium vanadata and 0.2% EDTA·2Na.

[Standards]

Direct-bilirubin-containing standard

An aqueous solution containing ditaurobilirubin in an amount corresponding to 10 mg/dl of bilirubin was used as a direct-bilirubin-containing standard.

Indirect-bilirubin-containing standard

Commercially available bilirubin standard serum (containing 10 mg/dl of indirect bilirubin, available from Wako Pure Chemical Industries, Ltd.) was used as an indirect-bilirubin-containing standard.

[Procedure]

The same as in Experimental Example 1.

[Results]

The results obtained are shown in Tables 3-1 and 3-2. For reference, in Tables 3-1 and 3-2 are also shown measured values of direct bilirubin concentration in fresh human serum which were obtained by using a combination of each first reagent solution and each second reagent solution, or a commercially available reagent for measuring bilirubin [Bilirubin II-HA Test Wako (mfd. by Wako Pure Chemical Industries, Ltd., diazo method)].

TABLE 3-1

| | (vanadic acid method) | | | | |
|---|---|---|---|---|---|
| Reaction inhibitor | Concentration | Blank value | Direct bilirubin-containing standard | Indirect-bilirubin-containing standard | Measured value for serum mg/dl |
| | | | OD (505 nm/450 nm) | | |
| — | — | 0.086 | 0.259 | 0.241 | 4.8 |
| Triton X-405 | 0.3% | 0.082 | 0.276 | 0.061 | 3.7 |
| Hydrazine hydrochloride | 20 mm | 0.020 | 0.270 | 0.037 | 3.4 |
| Hydroxylamine hydrochloride | 20 mM | 0.018 | 0.268 | 0.024 | 3.2 |
| Tetraethylenepentamine | 20 mM | 0.110 | 0.278 | 0.053 | 3.5 |
| Acetamidophenol | 20 mm | 0.061 | 0.270 | 0.071 | 3.6 |
| Polyvinyl alcohol | 0.3% | 0.082 | 0.277 | 0.037 | 3.4 |
| Triton X-405 / Hydrazine hydrochloride | 0.3% / 20 mM | 0.006 | 0.266 | 0.017 | 3.3 |
| Triton X-405 / Hydroxylamine hydrochloride | 0.3% / 20 mM | 0.003 | 0.261 | 0.013 | 3.3 |
| Diazo method | — | — | — | — | 3.4 |

TABLE 3-2

| | (manganese method) | | | | |
|---|---|---|---|---|---|
| Reaction inhibitor | Concentration | Blank value | Direct bilirubin-containing standard | Indirect-bilirubin-containing standard | Measured value for serum mg/dl |
| | | | OD (505 nm/450 nm) | | |
| — | — | 0.030 | 0.272 | 0.238 | 6.4 |
| Triton X-405 | 0.3% | 0.009 | 0.256 | 0.015 | 3.4 |

TABLE 3-2-continued (manganese method)

| Reaction inhibitor | Concentration | Blank value | Direct bilirubin-containing standard OD (505 nm/450 nm) | Indirect-bilirubin-containing standard | Measured value for serum mg/dl |
|---|---|---|---|---|---|
| Salicyladoxime | 20 mM | | | | |
| Triton X-405 | 0.3% | 0.005 | 0.247 | 0.006 | 3.3 |
| Acetoxime | 20 mM | | | | |
| Triton X-405 | 0.3% | 0.003 | 0.243 | 0.014 | 3.3 |
| P-Acetamidophenol | 20 mM | | | | |
| Triton X-405 | 0.3% | 0.026 | 0.205 | 0.050 | 3.5 |
| Tetraethylenepentamine | 20 mM | | | | |
| Diazo method | — | — | — | — | 3.4 |

As is clear from the results shown in Tables 3-1 and 3-2, the oxidation of indirect bilirubin was inhibited by the presence of one or two compounds selected from the group consisting of the hydrazine derivative, hydroxylamine derivative, oximes, aliphatic polyvalent amine, phenol, water-soluble high polymer and nonionic surfactant having a MLB value of 15 or more.

Although a mechanism by which the above compounds inhibit the oxidation of indirect bilirubin is not clear, the following mechanisms, for example, are thought of. Compounds having reducing ability, such as the hydrazine derivative, hydroxylamine derivative, oximes, aliphatic polyvalent amine and phenol absorb the surplus oxidizing agent and hence prevent the gradual oxidation of indirect bilirubin. Compounds such as the water-soluble high polymer and the nonionic surfactant having a HLB value of 15 or more combine with indirect bilirubin in some way or other to prevent the oxidation of indirect bilirubin, so that they improve the specificity for direct bilirubin of the oxidizing agent.

Example 1

[Reagent solutions]

First reagent solution (for measuring direct bilirubin)

As a first reagent solution for measuring direct bilirubin, there was used 0.1M citric acid-sodium citrate buffer (pH 3.0) containing 20 mM hydroxylamine hydrochloride and 0.2% EDTA·2Na.

First reagent solution (for measuring total bilirubins)

As a first reagent solution for measuring total bilirubins, there was used 0.1M citric acid-sodium citrate buffer (pH 3.0) containing 0.3% cetyltrimethylammonium bromide, 0.3% Amphitol 24B (a trade name, Kao Corp.) and 0.2% EDTA·2Na.

Second reagent solution

As a second reagent solution, there was used 0.01M phosphate buffer (pH 6.0) containing 3 mM sodium vanadate and 0.2% EDTA·2Na.

[Standards]

Direct-bilirubin-containing standard

An aqueous solution containing ditaurobilirubin in an amount corresponding to 10 mg/dl of bilirubin was used as a direct-bilirubin-containing standard.

Indirect-bilirubin-containing standard

Commercially available bilirubin standard serum (containing 10 mg/dl of indirect bilirubin, available from Wako Pure Chemical Industries, Ltd.) was used as an indirect-bilirubin-containing standard.

[Samples]

Forty fresh known sera were used as samples.

[Procedure]

The same as in Experimental Example 1.

Referential Example 1

For the same samples as used in Example 1, total bilirubins and direct bilirubin were measured by use of a commercially available reagent for measuring bilirubin [Bilirubin II-HA Test Wako (mfd. by Wako Pure Chemical Industries, Ltd., diazo method)]. The measurement was carried out according to the standard procedure described in a mannual attached to the above commercial reagent.

[Results]

Figure 1:
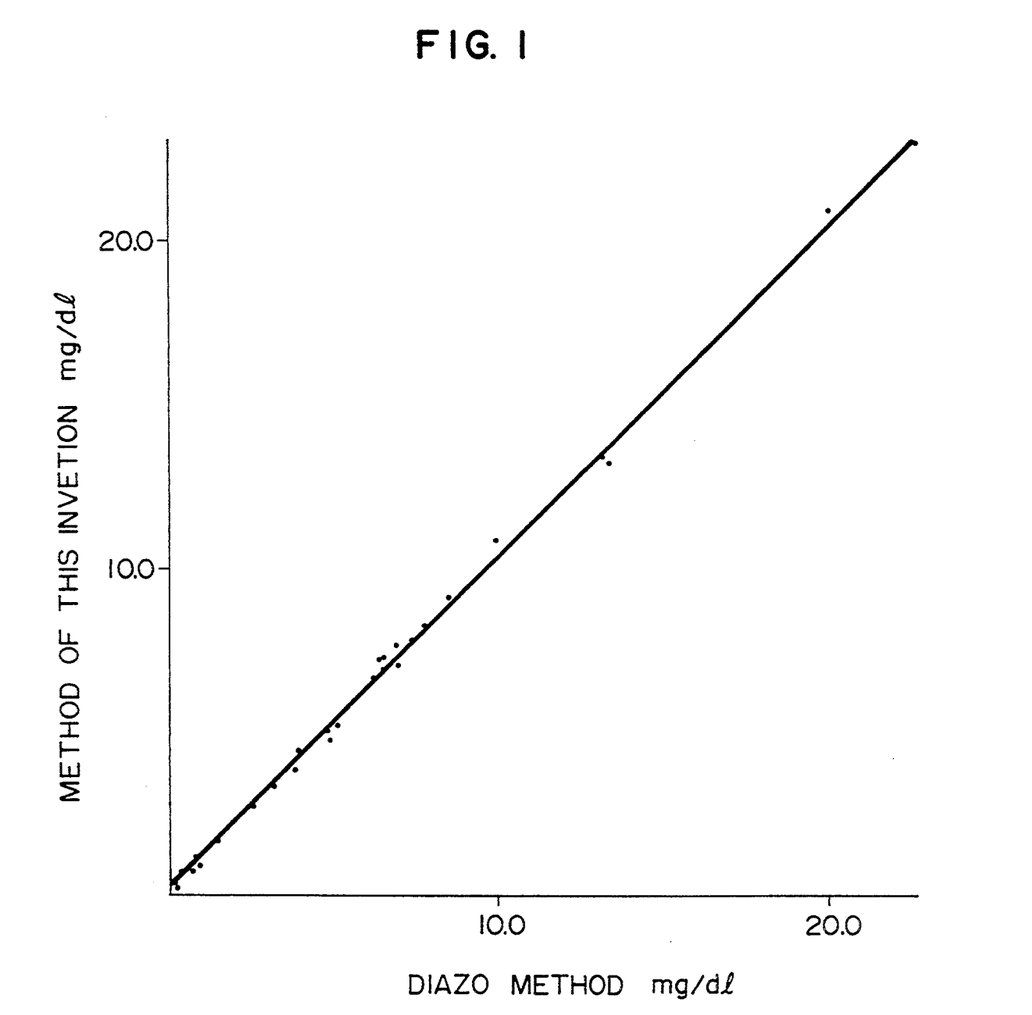
FIG. 1 shows a correlation graph for total bilirubins, and FIG. 2 that for direct bilirubin.
Figure 2:
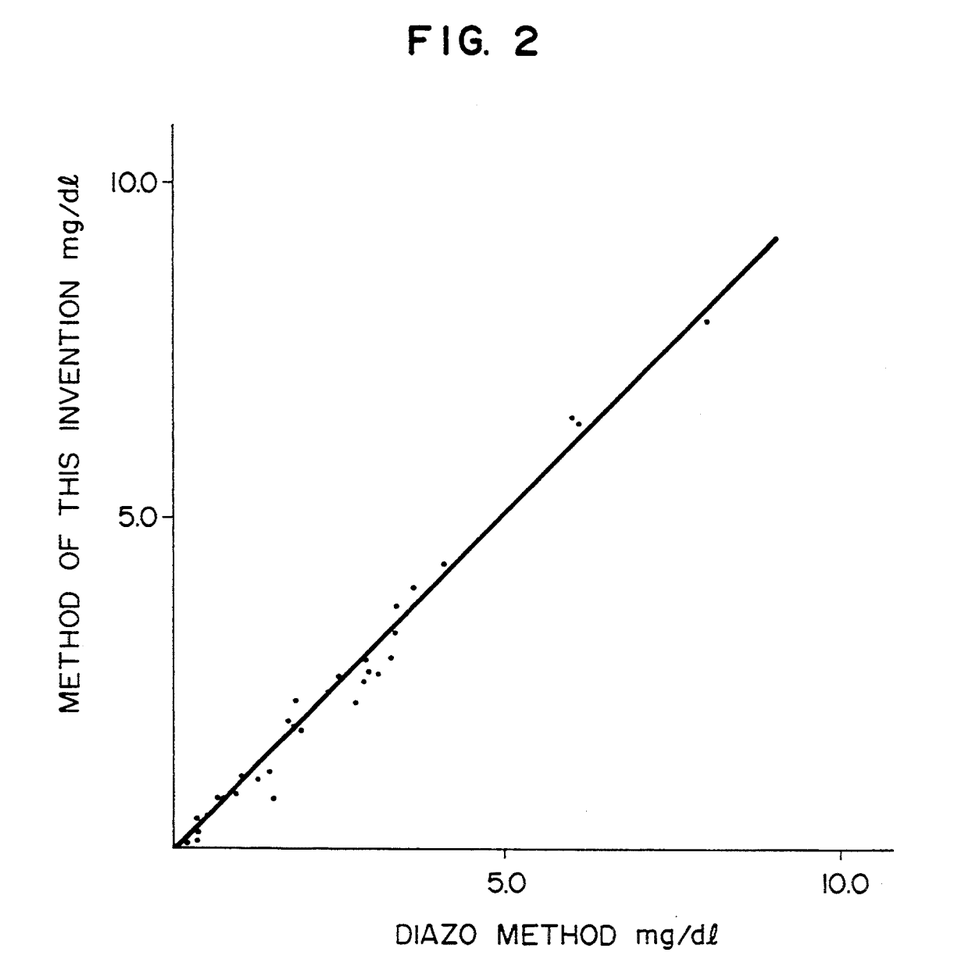

A correlation graph for total bilirubins and a correlation graph for direct bilirubin which were obtained on the basis of measured values obtained by Example 1 and Referential Example 1, are shown in FIG. 1 and FIG. 2, respectively. Correlation coefficients and regression line formulas which were obtained by processing the measured values stastically are as follows.

Total bilirubins

Correlation coefficient: $\gamma = 0,999$

Regression line formula: $Y = 1.017X + 0.250$ wherein Y: the measured value of total bilirubins which was obtained by Example 1.

X: the measured value of total bilirubins which was obtained by Referential Example 1.

Direct bilirubin

Correlation coefficient: $\gamma = 0.990$

Regression line formula: $Y = 1.021X - 0.003$ wherein Y: the measured value of direct bilirubin which was obtained by Example 1.

X: the measured value of direct bilirubin which was obtained by Referential Example 1.

As is clear from the above results, the measured values obtained by the method of this invention were in good correlation with those obtained by the conventional method (the diazo method).

Table 4 shows the results of measuring bilirubin concentrations in samples containing ascorbic acid, by the same procedure as above by using the reagent solutions described in Example 1 or the reagent described in Referential Example 1.

TABLE 4

| | Origin of reagent solution(s) | | | |
|---|---|---|---|---|
| | Example 1 | | Referential Example 1 | |
| Amount L-ascorbic acid in a sample (mg/dl) | Total bilirubins | Direct bilirubin | Total bilirubins | Direct bilirubin |
| | mg/dl | | | |
| 0 | 11.1 | 3.5 | 11.2 | 3.5 |
| 10 | 11.0 | 3.6 | 11.1 | 3.4 |
| 20 | 11.1 | 3.5 | 10.8 | 3.3 |

TABLE 4-continued

| Amount L-ascorbic acid in a sample (mg/dl) | Origin of reagent solution(s) | | | |
|---|---|---|---|---|
| | Example 1 | | Referential Example 1 | |
| | Total bilirubins | Direct bilirubin | Total bilirubins | Direct bilirubin |
| | mg/dl | | | |
| 50 | 11.3 | 3.6 | 9.1 | 3.1 |
| 70 | 11.0 | 3.6 | 7.6 | 3.0 |
| 100 | 10.8 | 3.5 | 6.0 | 2.8 |

As is clear from the results shown in Table 4, the method of this invention is hardly affected by ascorbic acid present in a sample, as compared with the conventional method.

When calibration curves for total bilirubins and direct bilirubin, respectively, were prepared by use of the reagent solutions described in Example 1, both of them showed good linearlity up to 40 mg/dl.

Example 2

Measurement of direct bilirubin

[Reagent solutions]

First reagent solution

As a first reagent solution, there was used 0.1M citric acid-sodium citrate buffer (pH 3.0) containing 0.3% Triton X-405 (a trade name, Rohm and Haas Co.; HLB value 17.9), 20 mM hydroxylamine hydrochloride and 0.2% EDTA·2Na.

Second reagent solution

As a second reagent solution, there was used 0.01M phosphate buffer (pH 7.0) containing 3 mM sodium vanadate and 0.2% EDTA·2Na.

[Standard]

An aqueous solution containing ditaurobilirubin in an amount corresponding to 10 mg/dl of bilirubin was used as a direct-bilirubin-containing standard.

[Samples]

Thirteen human sera frozen and stored after collection were used as samples.

[Procedure]

The same as in Example 1.

[Results]

The measurement results are shown in Table 5.

Comparative Example 1

Measurement was carried out by the same procedure as in Example 2 by using the same reagents, reagent solutions and samples as in Example 2, except for using Triton X-100 (a polyoxyethylene isooctylphenyl ether, a trade name, Rohm and Haas Co.; HLB value 13.5) in place of Triton X-405 (a trade name, Rohm and Haas Co.; HLB 17.9) in the first reagent solution.

[Results]

Results obtained are also shown in Table 5.

Example 3

Measurement of direct bilirubin

[Reagent solutions]

First reagent solution

As a first reagent solution, there was used 0.1M citric acid-sodium citrate buffer (pH 3.6) containing 0.3% Triton X-405 (a trade name, Rohm and Haas Co.; HLB value 17.9), 0.5% thiourea and 0.2% EDTA·2Na.

Second reagent solution

A 5 mM aqueous copper sulfate solution was used as a second reagent solution.

[Standard]

The same standard as in Example 2 was used.

[Samples]

The same samples as in Example 2 were used.

[Procedure]

The same as in Example 1.

[Results]

The measurement results are also shown in Table 5.

Comparative Example 2

Measurement was carried out by the same procedure as in Example 3 by using the same reagents, reagent solutions and samples as in Example 3, except for using Triton X-100 (a polyoxyethylene isooctylphenyl ether, a trade name, Rohm and Haas Co.; HLB value 13.5) in place of Triton X-405 (a trade name, Rohm and Haas Co.; HLB value 17.9) in the first reagent solution.

[Results]

The measurement results are also shown in Table 5.

Referential Example 2

For the same samples as used in Example 2, direct bilirubin was measured by use of a commercially available reagent for measuring bilirubin [Bilirubin II-HA Test Wako (mfd. by Wako Pure Chemical Industries, Ltd., diazo method)]. The measurement was carried out according to the standard procedure described in a manual attached to the above commercial reagent.

[Results]

The measurement results are also shown in Table 5.

TABLE 5

| Sample No. | Direct bilirubin concentration (mg/dl) | | | | |
|---|---|---|---|---|---|
| | Example 2 | Comparative Example 1 | Example 3 | Comparative Example 2 | Referential Example 2 |
| 1 | 0.5 | 0.5 | 0.6 | 0.7 | 0.5 |
| 2 | 0.8 | 0.8 | 0.9 | 0.8 | 0.7 |
| 3 | 0.2 | 0.2 | 0.3 | 0.3 | 0.2 |
| 4 | 0.8 | 1.5 | 1.0 | 2.4 | 1.1 |
| 5 | 4.8 | 4.8 | 4.7 | 4.8 | 4.6 |
| 6 | 1.6 | 1.6 | 1.7 | 1.9 | 1.3 |
| 7 | 2.9 | 3.9 | 2.7 | 4.0 | 2.6 |
| 8 | 1.9 | 2.4 | 1.7 | 2.7 | 2.1 |
| 9 | 2.0 | 2.8 | 2.0 | 3.2 | 2.2 |
| 10 | 2.1 | 2.5 | 2.1 | 3.2 | 2.3 |
| 11 | 2.2 | 2.8 | 2.1 | 3.3 | 2.2 |
| 12 | 2.5 | 2.7 | 2.4 | 3.0 | 2.5 |
| 13 | 3.1 | 4.0 | 3.1 | 3.9 | 2.7 |

Table 6 shows correlation coefficients and regression line formulas which were obtained by statistical processing of the direct bilirubin concentrations of the individual samples which were obtained by Referential Example 2 and those obtained by each of Example 2, Example 3, Comparative Example 1 and Comparative Example 2.

TABLE 6*

| Origin of Y | Correlation coefficient | Regression line formula |
|---|---|---|
| Example 2 | 0.985 | Y = 1.050X − 0.065 |
| Comparative Example 1 | 0.958 | Y = 1.144x + 0.147 |
| Example 3 | 0.980 | Y = 0.978X + 0.066 |
| Comparative Example 2 | 0.943 | Y = 1.104X + 0.508 |

*In all the cases, X is the measured value obtained by Referential Example 2.

As is clear from the results shown in Table 5 and Table 6, the measured values of direct bilirubin obtained by using Triton X-405 (a trade name, Rohm and Haas Co.) having a HLB value of 15 or more as the reaction inhibitor were in good correlation with those obtained by the diazo method, but the measured values of direct bilirubin obtained by using Triton X-100 (a trade name, Rohm and Haas Co.) having a HLB value of less than 15 in place of Triton X-405 (a trade name, RoLm and Haas Co.) were poor correlation with those obtained by the diazo method.

As is clear from the facts described above, this invention is characterized in that vanadic acid ions or manganese (III) ions are used as an oxidizing agent for bilirubin, and that for measuring direct bilirubin, at least one compound selected from the group consisting of hydrazine derivatives, hydroxylamine derivatives, oximes, aliphatic polyvalent amines, phenols, water-soluble high polymers, and nonionic surfactants having a HLB value of 15 or more is used as the reaction inhibitor. This invention provides a method for measuring bilirubin which is free from all of the problems in conventional methods, for example, their low applicability to an automatic analyzer, their poor correlation with the diazo method, and the low stability of reagent solutions.

What is claimed is:

1. A method for measuring the amount of total bilirubin in a fluid containing bilirubin, which comprises:
   adding to the fluid a first reagent solution containing a reaction accelerator for accelerating the oxidation of bilirubin,
   measuring an optical change of the fluid to which the first reagent solution has been added,
   adding a second reagent solution containing vanadic acid ions as a chemical oxidizing agent for bilirubin, to the fluid to which the first reagent solution has been added,
   measuring an optical change of the fluid to which the first and second reagent solutions have been added,
   calculating the amount of total bilirubin in the fluid from said optical changes.

2. A method according to claim 1, wherein a chelating agent is contained in the first reagent solution, the second reagent solution or both the first and second reagent solutions.

3. A method according to claim 1, wherein the reaction accelerator is an anionic surfactant, a cationic surfactant or an amphoteric surfactant.

4. A method for measuring the amount of direct bilirubin in a fluid containing bilirubin, which comprises:
   adding to the fluid a reagent solution comprising vanadic acid ions as a chemical oxidizing agent and at least one reaction inhibitor, selected from the group consisting of hydrazine derivatives, hydroxylamine derivatives, oximes, aliphatic polyvalent amines, phenols, water-soluble high polymers and nonionic surfactants having a HLB value of 15 or more, for inhibiting the oxidation of indirect bilirubin, and
   measuring an optical change of the fluid to which the reagent solution has been added and calculating the amount of direct bilirubin in the fluid from said optical change.

5. A method according to claim 4, wherein the reagent solution further comprises a chelating agent.

6. A method for measuring the amount of direct bilirubin in a fluid containing bilirubin, which comprises:
   adding to the fluid a first reagent solution containing a reaction inhibitor for inhibiting the oxidation of indirect bilirubin,
   measuring an optical change of the fluid to which the first reagent solution has been added,
   adding a second reagent solution containing vanadic acid ions as a chemical oxidizing agent for bilirubin to the fluid to which the first reagent solution has been added,
   measuring an optical change of the fluid to which the first and second reagent solutions have been added, and
   calculating the amount of direct bilirubin in the fluid from said optical changes.

7. A method according to claim 6, wherein the reaction inhibitor is at least one compound selected from the group consisting of hydrazine derivatives, hydroxylamine derivatives, oximes, aliphatic polyvalent amines, phenols, water-soluble high polymers, and nonionic surfactants having a HLB value of 15 or more.

8. A method according to claim 7, wherein a chelating agent is contained in the first reagent solution, the second reagent solution or both the first and second reagent solutions.

9. A kit for measuring the amount of total billrubin comprising a first reagent solution comprising a reaction accelerator, and a second reagent solution comprising vanadic acid ions as a chemical oxidizing agent for bilirubin.

10. A kit according to claim 9, wherein a chelating agent is contained in the first reagent solution, the second reagent solution or both the first and second reagent solutions.

11. A kit for measuring the amount of direct bilirubin comprising:
    a first reagent solution comprising at least one reaction inhibitor selected from the group consisting of hydrazine derivatives, hydroxylamine derivatives, oximes, aliphatic polyvalent amines, phenols, water-soluble high polymers, and nonionic surfactants having a HLB value of 15 or more for inhibiting the oxidation of indirect bilirubin, and
    a second reagent solution comprising vanadic acid ions as a chemical oxidizing agent.

12. A kit according to claim 11, wherein a chelating agent is contained in the first reagent solution, the second reagent solution or both the first and second reagent solutions.

13. A method for measuring the amount of total bilirubin in a fluid containing bilirubin, which comprises:
    adding to the fluid a first reagent solution essentially consisting of a buffer and a reaction accelerator for accelerating the oxidation of bilirubin,
    measuring an optical change of the fluid to which the first reagent solution has been added,
    adding a second reagent solution essentially consisting of vanadic acid ions as a chemical oxidizing agent for bilirubin, to the fluid to which the first reagent solution has been added,
    measuring an optical change of the fluid to which the first and second reagent solutions have been added,
    calculating the amount of total bilirubin in the fluid from said optical changes.

14. A method for measuring the amount of total bilirubin in a fluid containing bilirubin, which comprises:
    adding to the fluid a first reagent solution essentially consisting of a buffer, a reaction accelerator for accelerating the oxidation of bilirubin and a chelating agent,
    measuring an optical change of the fluid to which the first reagent solution has been added,
    adding a second reagent solution essentially consisting of vanadic acid ions as a chemical oxidizing agent for bilirubin, to the fluid to which the first reagent solution has been added,
    measuring an optical change of the fluid to which the first and second reagent solutions have been added, calculating the amount of total bilirubin in the fluid from said optical changes.

15. A method for measuring the amount of total bilirubin in a fluid containing bilirubin, which comprises:
  adding to the fluid a first reagent solution essentially consisting of a buffer and a reaction accelerator for accelerating the oxidation of bilirubin,
  measuring an optical change of the fluid to which the first reagent solution has been added,
  adding a second reagent solution essentially consisting of vanadic acid ions as a chemical oxidizing agent for bilirubin and a chelating agent, to the fluid to which the first reagent solution has been added,
  measuring an optical change of the fluid to which the first and second reagent solutions have been added.
  calculating the amount of total bilirubin in the fluid from said optical changes.

16. A method for measuring the amount of total bilirubin in a fluid containing bilirubin, which comprises:
  adding to the fluid a first reagent solution essentially consisting of a buffer, a reaction accelerator for accelerating the oxidation of bilirubin and a chelating agent,
  measuring an optical change of the fluid to which the first reagent solution has been added,
  adding a second reagent solution essentially consisting of vanadic acid ions as a chemical oxidizing agent for bilirubin and a chelating agent, to the fluid to which the first reagent solution has been added,
  measuring an optical change of the fluid to which the first and second reagent solutions have been added,
  calculating the amount of total bilirubin in the fluid from said optical changes.

17. A method for measuring the amount of total bilirubin in a fluid containing bilirubin, which comprises:
  adding to the fluid a first reagent solution essentially consisting of a buffer and a reaction accelerator for accelerating the oxidation of bilirubin,
  measuring an optical change of the fluid to which the first reagent solution has been added,
  adding a second reagent solution essentially consisting of a buffer and vanadic acid ions as a chemical oxidizing agent for bilirubin, to the fluid to which the first reagent solution has been added,
  measuring an optical change of the fluid to which the first and second reagent solutions have been added,
  calculating the amount of total bilirubin in the fluid from said optical changes.

18. A method for measuring the amount of total bilirubin in a fluid containing bilirubin, which comprises:
  adding to the fluid a first reagent solution essentially consisting of a buffer, a reaction accelerator for accelerating the oxidation of bilirubin and a chelating agent,
  measuring an optical change of the fluid to which the first reagent solution has been added,
  adding a second reagent solution essentially consisting of a buffer and vanadic acid ions as a chemical oxidizing agent for bilirubin, to the fluid to which the first reagent solution has been added,
  measuring an optical change of the fluid to which the first and second reagent solutions have been added,
  calculating the amount of total bilirubin in the fluid from said optical changes.

19. A method for measuring the amount of total bilirubin in a fluid containing bilirubin, which comprises:
  adding to the fluid a first reagent solution essentially consisting of a buffer and a reaction accelerator for accelerating the oxidation of bilirubin,
  measuring an optical change of the fluid to which the first reagent solution has been added,
  adding a second reagent solution essentially consisting of a buffer, vanadic acid ions as a chemical oxidizing agent for bilirubin and a chelating agent, to the fluid to which the first reagent solution has been added,
  measuring an optical change of the fluid to which the first and second reagent solutions have been added,
  calculating the amount of total bilirubin in the fluid from said optical changes.

20. A method for measuring the amount of total bilirubin in a fluid containing bilirubin, which comprises:
  adding to the fluid a first reagent solution essentially consisting of a buffer, a reaction accelerator for acceleration the oxidation of bilirubin and a chelating agent,
  measuring an optical change of the fluid to which the first reagent solution has been added,
  adding a second reagent solution essentially consisting of a buffer, vanadic acid ions as a chemical oxidizing agent for bilirubin and a chelating agent, to the fluid to which the first reagent solution has been added,
  measuring an optical change of the fluid to which the first and second reagent solutions have been added,
  calculating the amount of total bilirubin in the fluid from said optical changes.

21. A method for measuring the amount of total bilirubin in a fluid containing bilirubin, which comprises:
  adding to the fluid a first reagent solution essentially consisting of a buffer, a reaction accelerator for accelerating the oxidation of bilirubin, a chelating agent and an antiseptic,
  measuring an optical change of the fluid to which the first reagent solution has been added,
  adding a second reagent solution essentially consisting of vanadic acid ions as a chemical oxidizing agent for bilirubin, a chelating agent and an antiseptic to the fluid to which the first reagent solution has been added,
  measuring an optical change of the fluid to which the first and second reagent solutions have been added,
  calculating the amount of total bilirubin in the fluid from said optical changes.

* * * * *